(12) United States Patent
Patel et al.

(10) Patent No.: US 10,456,418 B2
(45) Date of Patent: Oct. 29, 2019

(54) PREPARATION OF PHARMACEUTICAL DOSAGE FORMS CONTAINING IRON (III) SALTS

(71) Applicants: Mahendra R. Patel, Milltown, NJ (US); Shrenik K. Shah, Metuchen, NJ (US)

(72) Inventors: Mahendra R. Patel, Milltown, NJ (US); Shrenik K. Shah, Metuchen, NJ (US)

(73) Assignee: Navinta, LLC, Ewing, NJ (US)

(*) Notice: Subject to any disclaimer, the term of this patent is extended or adjusted under 35 U.S.C. 154(b) by 0 days.

(21) Appl. No.: 15/286,226

(22) Filed: Oct. 5, 2016

(65) Prior Publication Data

US 2017/0095509 A1 Apr. 6, 2017

Related U.S. Application Data

(60) Provisional application No. 62/237,359, filed on Oct. 5, 2015.

(51) Int. Cl.
| | | |
|---|---|---|
| *A61K 33/26* | (2006.01) | |
| *A61K 9/08* | (2006.01) | |
| *A61K 33/42* | (2006.01) | |
| *A61K 31/194* | (2006.01) | |
| *G16C 20/10* | (2019.01) | |

(52) U.S. Cl.
CPC ............... *A61K 33/26* (2013.01); *A61K 9/08* (2013.01); *G16C 20/10* (2019.02)

(58) Field of Classification Search
None
See application file for complete search history.

(56) References Cited

U.S. PATENT DOCUMENTS

| | | |
|---|---|---|
| 7,816,404 B2 | 10/2010 | McCall, Jr. |
| 8,178,709 B2 | 5/2012 | Nelson et al. |
| 2006/0045905 A1 | 3/2006 | Ozeki et al. |
| 2007/0012622 A1 | 1/2007 | Wash |
| 2011/0021629 A1* | 1/2011 | Nelson ................ A61K 31/194 514/502 |

FOREIGN PATENT DOCUMENTS

| | | |
|---|---|---|
| EP | 2497380 A1 | 9/2012 |
| WO | 2006130027 A1 | 12/2006 |
| WO | 2013167506 A1 | 11/2013 |
| WO | 2015028272 A1 | 3/2015 |

OTHER PUBLICATIONS

Caspari (Treatise on Pharmacy for Students & Pharmacists, Lea Brothers & Co., 1906, pp. 556-557) (Year: 1906).*

* cited by examiner

*Primary Examiner* — Bethany P Barham
*Assistant Examiner* — Peter Anthopolos
(74) *Attorney, Agent, or Firm* — St. Onge Steward Johnston & Reens LLC

(57) ABSTRACT

The present invention provides a method for designing a ferric pyrophosphate citrate complex composition containing pyrophosphate, citrate, ferric, sodium, and sulfate ions and calculating and adjusting each salt needed based on a choice of salts that contain the above ions and a desired concentration of each ion in the final product. The present invention also provides a process for preparing a pharmaceutical dosage form of ferric pyrophosphate citrate complex composition in liquid form which is ready to be administrated to patients in need and which maintains the mass balance of ion sources throughout the process.

13 Claims, 3 Drawing Sheets

PREPARATION OF PHARMACEUTICAL DOSAGE FORMS CONTAINING IRON (III) SALTS

FIELD OF THE INVENTION

The present invention relates to the preparation of pharmaceutical dosage forms containing iron (III) salts.

BACKGROUND OF THE INVENTION

Iron plays an essential role in many biological processes. Complexes of iron with biomolecules are required for many vital physiologic processes, such as transport of oxygen throughout the body, synthesis of hormones, metabolism, detoxification and electron transport. It is recognized that iron deficiency can lead to many serious pathological conditions. Public health authorities recommend iron supplementation to avoid anemia caused by iron deficiency. Many forms of supplements, from elemental iron, to various salts and complexes of iron are used for oral administration.

In more severe cases of anemia, such as in patients with chronic diseases and patients undergoing dialysis, iron supplements in solution are provided by intravenous route. Many of these iron compounds have complex structures where iron atoms are held in a core surrounded by organic or inorganic moieties. Although most of these iron complexes have been known for a long time, commercial production of these compounds has been challenging and has required extensive technological developments. Typically these complexes are first made and isolated as solid and then made into a dosage form as a solution. However, the processes that involve isolation of the solid complex do not provide a product of uniform composition.

U.S. Pat. No. 7,816,404 discloses a process of preparing a water soluble ferric pyrophosphate citrate chelate by precipitating it from a liquid composition. Experimental details in Table 11 of U.S. Pat. No. 7,816,404 reveal that the solid ferric pyrophosphate citrate chelate takes about 60% by weight of the liquid composition. Extra $Fe^{3+}$ may be in the form of other salts, impurities, or remains in mother liquor and thus lost in the liquid composition. The precipitated ferric pyrophosphate citrate chelate needs to be dried in an oven. Extra precautions are required during the drying to minimize decomposition of the chelate such as conversion of pyrophosphate to phosphate due to heat. It is reported that the chelate contains phosphate in an amount of 2% or less by weight.

The process disclosed in U.S. Pat. No. 7,816,404 cannot provide a product of uniform composition. Based on the data provided in Tables 10 and 11 of U.S. Pat. No. 7,816,404, we calculate percent of variations of citrate and pyrophosphate in different lots, shown as below:

| Batch No. | Scale | % Fe Assay[1] | % Citrate Assay[1] | % Citrate Variance[2] | % Pyrophosphate Assay[1] | % Pyrophosphate Variance[2] |
|---|---|---|---|---|---|---|
| 4864 | 1 g | 8.6 | 28.1 | +6.22 | 11.8 | −8.24 |
| 4865 | 2 g | 8.8 | 37.5 | +15.03 | 12.7 | −7.81 |
| 4866 | 2 g | 10.2 | 32.6 | +6.55 | 13.8 | −9.97 |
| 4868 | 10 g | 9.6 | 30.3 | +5.78 | 14.1 | −8.27 |
| 4869 | 10 g | 9.7 | 27.7 | +3.02 | 13.2 | −9.405 |
| 511516 | 10 g | 10.83 | 22.4 | −5.16 | 18.3 | −6.94 |
| 511517 | 10 g | 10.27 | 23.5 | −2.63 | 17.3 | −6.63 |
| 511913 | 25 g | 10.23 | 23.4 | −2.63 | 17.7 | −6.14 |

[1]Weight percents shown here are from the specific Batch No. in Tables 10 and 11 of Pat. No. 7,816,404.
[2]Variance in citrate and pyrophosphate content is the difference in percent composition of isolated solid from the expected amount for $Fe_4(citrate)_3(pyrophosphate)_3$ on the basis of assay for % Fe. It is marked as "+" if weight percent in the sample is more than expected and marked as "−" if weight percent in sample is less than expected.

The above calculations show that even when the assay for % Fe for the lots are similar, there are big differences in citrate and pyrophosphate content from lot to lot. Actually on scale up, the citrate goes from excess to deficiency, even though the same excess of citrate is used in the chemical reaction. It is obvious from these data that further scale up to commercial scale will be very challenging.

Without wishing to be bound by theory, the inconsistency in net output with scale given same input, as observed in the prior art process, may be caused by loss on drying and degradation (e.g., from pyrophosphate to phosphate) due to heat, as required by the process of U.S. Pat. No. 7,816,404.

U.S. Pat. No. 8,178,709 reports a method of preparation of a water soluble ferric citrate chelate with varying amounts of pyrophosphate and sodium, which indicates that non-essential components make up a significant weight of the bulk mass. This material is prepared by air oxidation of $Fe^{2+}$ to $Fe^{3+}$ and requires 3-7 days to complete the reaction in laboratory. The composition that enables the oxidation is essentially free of sulfate. Because the product is light sensitive, the oxidation process has to be run in dark. Given the long reaction time, scaling up the oxidation process for commercial production is very challenging and requires many operational controls.

Therefore, there is a need for an operationally simple procedure for preparing solutions of iron salt that can readily be administered.

SUMMARY OF THE INVENTION

The inventors of this application have found a way to avoid isolating the solid of iron (III) containing complex during a manufacturing process. In one aspect, the present invention provides a process of directly preparing a dosing solution containing a soluble form of iron (III). The dosing solution may contain an iron (III) concentration of between 10-250 mM. The iron (III) solution may be further diluted if needed.

One novel feature of the process is that the mass balance is maintained because all the components of a final product mixture containing ferric pyrophosphate citrate complex and other salts are same in mass balance as input material. As a result, the process is suitable for scaling up the production of the final product mixture.

Because the mass balance of the input material is maintained in the final product with respect to each ion, it is possible to design the iron (III) containing complex and/or calculate the actual percent of each ion in the final product.

In another aspect, the present invention provides a method for designing a ferric pyrophosphate citrate complex composition containing pyrophosphate, citrate, ferric, sodium, and sulfate ions and calculating each salt needed based on a choice of salts that contain the above ions and a desired concentration of each ion in the final product. The present invention may further provide a process for preparing a ferric pyrophosphate citrate complex composition by incorporating the design method.

In yet another aspect, the present invention provides a method for determining ion concentrations of a ferric pyrophosphate citrate complex composition based on the actual weight of each salt added in the composition and percent by weight of each ion in each salt.

In a further aspect, the present invention provides a method for adjusting the amount of each salt needed to make a ferric pyrophosphate citrate complex composition so that each ion falls in a preset range by incorporating the design method and the method for determining ion concentrations of a ferric pyrophosphate citrate complex composition.

DETAILED DESCRIPTION OF THE INVENTION

Figure 1:
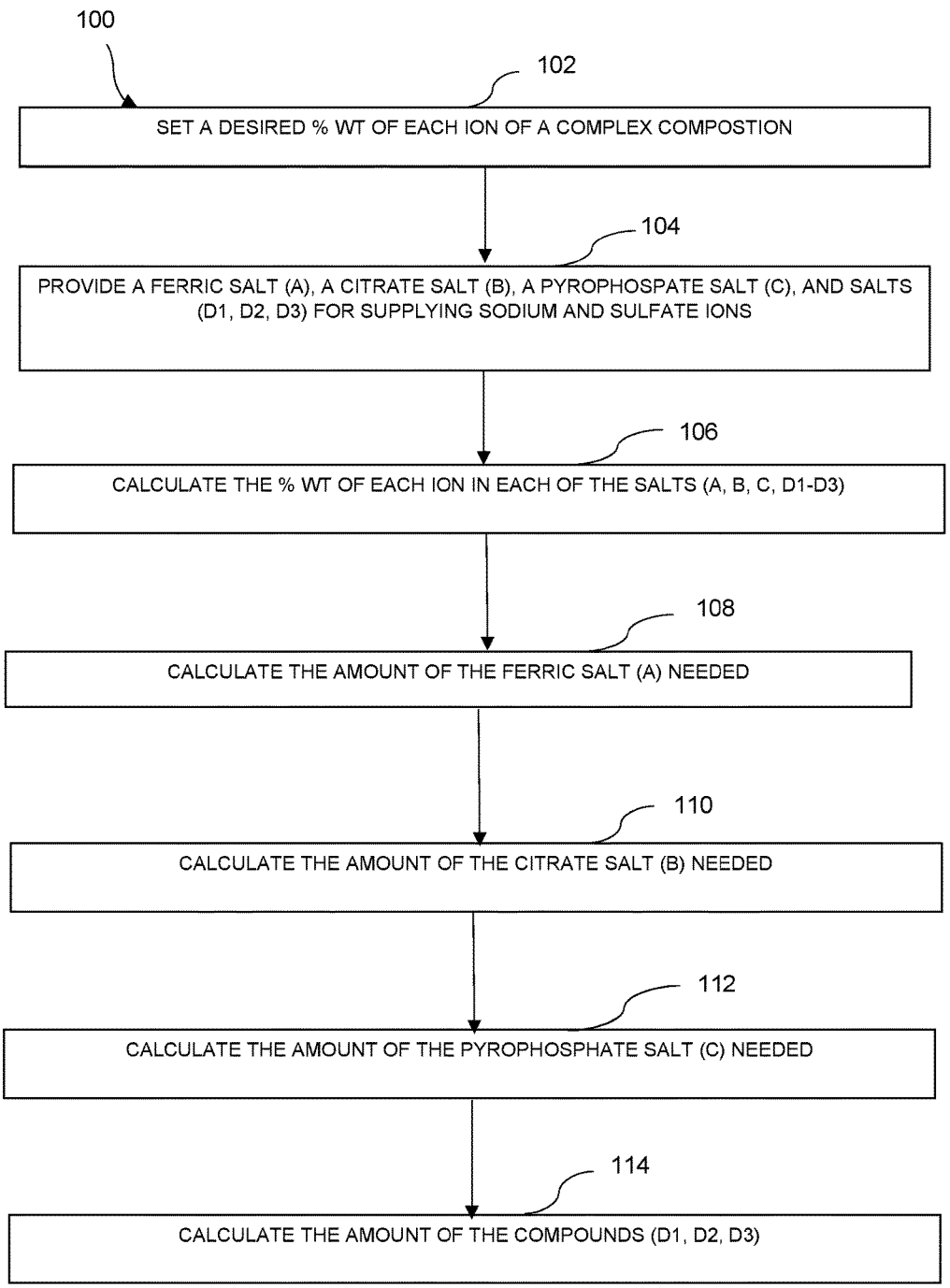
FIG. 1 is a schematic view of a method for designing a ferric pyrophosphate citrate complex composition containing pyrophosphate, citrate, ferric, sodium, and sulfate ions.

In one aspect, the present invention provides a process of directly preparing a dosing solution containing a soluble form of iron (III) at a concentration of between about 10-250 mM. By the term "mM", it refers to a concentration unit of milimole/liter (i.e., $1 \times 10^{-3}$ mol/L).

The process comprises the steps of: mixing a citrate ion source, a pyrophosphate ion source, and a ferric (i.e., iron (III)) ion source in an aqueous based vehicle carrier to form a solution of a ferric pyrophosphate citrate complex, without isolating a solid form of ferric pyrophosphate citrate complex. In other words, the ferric pyrophosphate citrate complex remains in solution throughout the process and can be directly used as a dosage form, with or without a further dilution. In some embodiments, the process comprises the step of mixing a sodium ion source, wherein the number of sodium ions in a molecule of sodium ion source is 1, 2, 3, or 4. For example, monosodium citrate contains one (1) sodium ion; disodium citrate contains two (2) sodium ions, trisodium citrate contains three (3) sodium ions; tetrasodium pyrophosphate contains four (4) sodium ions. In some other embodiments, the process further comprises the step of mixing a sulfate ion source. A ferric pyrophosphate citrate complex is formed when all of the relevant ions are added. The ferric pyrophosphate citrate complex comprises ferric, pyrophosphate, and citrate ions. Additionally, it may comprises sodium and sulfate ions.

Suitable ferric ion sources for the present invention include, but are not limited to, ferric sulfate, ferric sulfate hydrate, ferric chloride, ferric ammonium sulfate, a hydrate thereof, and a combination thereof. Suitable citrate ion sources may be selected from a group consisting of citric acid, monosodium citrate, disodium citrate, trisodium citrate, a hydrate thereof, and a combination thereof. Suitable pyrophosphate ion sources may be selected from a group consisting of disodium dihydrogen pyrophosphate, tetrasodium pyrophosphate, a hydrate thereof, and a combination thereof. Suitable sodium ion sources may include, but are not limited to, monosodium citrate, disodium citrate, trisodium citrate, disodium dihydrogen pyrophosphate, tetrasodium pyrophosphate, sodium hydroxide, sodium carbonate, sodium bicarbonate, sodium sulfate, and an applicable hydrate thereof. Suitable sulfate ion sources may include, but are not limited to, ferric sulfate, sodium sulfate, ferric ammonium sulfate, and a hydrate thereof. In one ferric pyrophosphate citrate complex composition, the sodium and sulfate ions may also be provided by up to three compounds which individually provides either sodium or sulfate ions.

According to some preferred embodiments, the ferric pyrophosphate citrate complex comprises a ferric ion in an amount from about 7.5 to about 9% by weight, a citrate ion in an amount from about 15 to about 22% by weight, a pyrophosphate ion in an amount from about 15 to about 22% by weight; a sodium ion in an amount from about 18 to about 25% by weight; and a sulfate ion in an amount of from about 20 to about 35% by weight. Unless stated otherwise, the percent by weight (% by wt.) used herein is based on an anhydrous basis of the total ions added into the composition.

In some embodiments, to mix the ions, it is preferable to prepare a ferric ion solution separately, and add the ferric ion solution to the rest of other ion solution. Because a ferric ion coexists with its counter ion in a salt, forming a ferric ion solution means to dissolve a ferric salt in a solvent. To facilitate the mixing, the resulting mixture may be heated up slightly above room temperature, for example, to about 50° C. and maintained at the temperature for a certain period of time, followed by cooling the solution to room temperature or below. To prevent degradation of the drug product, the solution temperature should not be raised too high or be kept at an elevated temperature for too long. The resulting mixture is preferably stored at room temperature or lower than room temperature. Prior to use, the resulting mixture may be diluted by adding water or an aqueous base solution to adjust pH thereof as well.

The process of the present invention provides an elegant way of making the desired final finished product drug composition without involving a precipitation with a solvent or a subsequent drying step. Thus, potential degradation of the drug complex is avoided. The prepared solution has no or essentially no phosphate ions. Additionally, the entire process is in situ and in one-pot (i.e., one unit operation, without the need to transfer reaction container). The prepared solution is ready for testing and may be directly used for filling of product through filtration into suitable containers. In contrast, the prior art process requires isolation, drying, and testing of a solid drug complex, followed by dissolution of the solid drug complex in water to prepare the desired dosage form. Thus, the process of the present invention is novel by using a one-solution phase processing to obtain a desired final drug formulation without isolation, drying, and additional solution preparation.

The drug complex composition prepared by the process has all citrate ions effectively used in forming the drug product complex. The yield and cost of the process is very economical given the nature of the process with a few number of steps involved and no loss of material in handing, compared to the prior art processes.

In another aspect, the present invention provides a pharmaceutical composition of a ferric pyrophosphate citrate complex prepared by the above mentioned process.

In yet another aspect, the present invention provides a method for treating iron deficiency comprising the step of administering to a subject in need a therapeutically effective amount of the ferric pyrophosphate citrate complex composition.

In a further aspect, the present invention provides a method for designing a ferric pyrophosphate citrate complex composition, a method for determining ion concentrations of a ferric pyrophosphate citrate complex composition, and a method for adjusting the amount of each salt needed to make a ferric pyrophosphate citrate complex composition so that each ion falls in a preset ion concentration range. The methods are derived from weight relationships of different ions and salts (i.e., ion sources) in the compositions.

According to one embodiment, an ionic composition of ferric citrate pyrophosphate comprises $Fe_2(SO_4)_3$, $Na_3$-Citrate, $Na_4$Pyrophosphate, and $Na_2SO_4$. The weight % of each ion in each salt can be summarized as follows:

| Name | Mol. Formula | Mol. Wt. | Percent | Percent |
|---|---|---|---|---|
| Ferric Sulfate | $Fe_2(SO_4)_3$ | 400.1 | 27.99% Fe | 72.01% $SO_4$ |
| Trisodium Citrate | $Na_3$-Citrate | 258.07 | 26.73% Na | 73.27% Citrate |
| Tetra sodium Pyrophosphate | $Na_4P_2O_7$ | 265.9 | 34.58% Na | 65.42% $P_4O_7$ |
| Sodium Sulfate | $Na_2SO_4$ | 142.1 | 32.37% Na | 67.63% $SO_4$ |

From the above table, one may calculate the amount of each ion in the final composition based on the amount of each salt used according to the following equations:

$$\text{Wt. Fe} = \text{Wt. Fe}_2(SO_4)_3 \times 0.2799 \quad (1)$$

$$\text{Wt. Citrate} = \text{Wt. Na}_3\text{-Citrate} \times 0.7327 \quad (2)$$

$$\text{Wt. P}_4O_7 = \text{Wt. Na}_4P_4O_7 \times 0.6542 \quad (3)$$

$$\text{Wt. Na} = \text{Wt. Na}_3\text{-Citrate} \times 0.2673 + \text{Wt. Na}_4P_4O_7 \times 0.3458 + \text{Wt. Na}_2SO_4 \times 0.3237 \quad (4)$$

$$\text{Wt. SO}_4 = \text{Wt. Fe}_2(SO_4)_3 \times 0.7201 + \text{Wt. Na}_2SO_4 \times 0.6763 \quad (5)$$

(wherein "X" means the operation "times"; wherein Wt. Fe means the weight of ferric ion; wherein Wt. $Fe_2(SO_4)_3$ means the weight of ferric sulfate, etc.).

One may further calculate percentage of each ion in the product according to the following equations:

$$\% \text{ Fe} = \text{Wt. Fe} \times 100/(\text{Wt. Fe}_2(SO_4)_3 + \text{Wt. Na}_3\text{-Citrate} + \text{Wt. Na}_4P_4O_7 + \text{Wt. Na}_2SO_4) \quad (6)$$

$$\% \text{ Citrate} = \text{Wt. Citrate} \times 100/(\text{Wt. Fe}_2(SO_4)_3 + \text{Wt. Na}_3\text{-Citrate} + \text{Wt. Na}_4P_4O_7 + \text{Wt. Na}_2SO_4) \quad (7)$$

$$\% \text{ P}_4O_7 = \text{Wt. P}_4O_7 \times 100/(\text{Wt. Fe}_2(SO_4)_3 + \text{Wt. Na}_3\text{-Citrate} + \text{Wt. Na}_4P_4O_7 + \text{Wt. Na}_2SO_4) \quad (8)$$

$$\% \text{ Na} = \text{Wt. Na} \times 100/(\text{Wt. Fe}_2(SO_4)_3 + \text{Wt. Na}_3\text{-Citrate} + \text{Wt. Na}_4P_4O_7 + \text{Wt. Na}_2SO_4) \quad (9)$$

$$\% \text{ SO}_4 = \text{Wt. SO}_4 \times 100/(\text{Wt. Fe}_2(SO_4)_3 + \text{Wt. Na}_3\text{-Citrate} + \text{Wt. Na}_4P_4O_7 + \text{Wt. Na}_2SO_4) \quad (10)$$

According to another embodiment, an ionic composition of ferric citrate pyrophosphate comprises $Fe_2(SO_4)_3$, $Na_2$-Citrate, $Na_4$Pyrophosphate, and $Na_2SO_4$. The weight % of each ion in each salt can be summarized as follows:

| Name | Mol. Formula | Mol. Wt. | Percent | Percent |
|---|---|---|---|---|
| Ferric Sulfate | $Fe_2(SO_4)_3$ | 400.1 | 27.99% Fe | 72.01% $SO_4$ |
| Disodium Citrate | $Na_2$-Citrate | 236 | 19.49% Na | 80.5% Citrate |
| Tetra sodium Pyrophosphate | $Na_4P_4O_7$ | 265.9 | 34.58% Na | 65.42% $P_4O_7$ |
| Sodium Sulfate | $Na_2SO_4$ | 142.1 | 32.37% Na | 67.63% $SO_4$ |

Using the information in the above table, one can calculate the amount of each component required in the final mixture for the desired composition by the following equations:

$$0.28 \times \text{Wt. Fe}_2(SO_4)_3 = (\text{desired Fe \%}/100) \times (\text{Wt. Fe}_2(SO_4)_3 + \text{Wt. Na}_2\text{-Citrate} + \text{Wt. Na}_4P_4O_7 + \text{Wt. Na}_2SO_4) \quad (11)$$

$$0.805 \times \text{Wt. Na}_2\text{-Citrate} = (\text{desired citrate \%}/100) \times (\text{Wt. Fe}_2(SO_4)_3 + \text{Wt. Na}_2\text{-Citrate} + \text{Wt. Na}_4P_4O_7 + \text{Wt. Na}_2SO_4) \quad (12)$$

$$0.654 \times \text{Wt. Na}_4P_4O_7 = (\text{desired P4O7\%}/100) \times (\text{Wt. Fe}_2(SO_4)_3 + \text{Wt. Na}_2\text{-Citrate} + \text{Wt. Na}_4P_4O_7 + \text{Wt. Na}_2SO_4) \quad (13)$$

$$0.72 \times \text{Wt. Fe}_2(SO_4)_3 + 0.676 \times \text{Wt. Na}_2SO_4 = (\text{desired SO}_4\%/100) \times (\text{Wt. Fe}_2(SO_4)_3 + \text{Wt. Na}_2\text{-Citrate} + \text{Wt. Na}_4P_4O_7 + \text{Wt. Na}_2SO_4) \quad (14)$$

$$0.195 \times \text{Wt. Na}_2\text{-Citrate} + 0.346 \times \text{Wt. Na}_4P_4O_7 + 0.324 \times \text{Wt. Na}_2SO_4 = (\text{desired Na \%}/100) \times (\text{Wt. Fe}_2(SO_4)_3 + \text{Wt. Na}_2\text{-Citrate} + \text{Wt. Na}_4P_4O_7 + \text{Wt. Na}_2SO_4) \quad (15)$$

The amounts of various salts needed can be calculated as follows based on the equations (11) to (13):

$$\text{Wt. Fe2(SO4)3} = (\text{desired Fe \%}/100)/0.28 \times (\text{Wt. Fe2(SO4)3} + \text{Wt. Na2-Citrate} + \text{Wt. Na4P4O7} + \text{Wt. Na2SO4})$$

$$\text{Wt. Na}_2\text{-Citrate} = (\text{desired citrate \%}/100)/0.805 \times (\text{Wt. Fe}_2(SO_4)_3 + \text{Wt. Na}_2\text{-Citrate} + \text{Wt. Na}_4P_4O_7 + \text{Wt. Na}_2SO_4)$$

$$\text{Wt. Na}_4P_4O_7 = (\text{desired P4O7\%}/100)/0.654 \times (\text{Wt. Fe}_2(SO_4)_3 + \text{Wt. Na}_2\text{-Citrate} + \text{Wt. Na}_4P_4O_7 + \text{Wt. Na}_2SO_4)$$

The amount of $Na_2SO_4$ may be calculated based on the equations (14) and (15).

Accordingly, the present invention provides a method for designing a ferric pyrophosphate citrate complex composition as illustrated in FIG. 1. The method 100 comprises the steps of:

(1) setting a desired percent by weight of each ion (step 102);

(2) providing one ferric salt (A) for supplying ferric ion, one citrate salt (B) for supplying citrate ion, one pyrophosphate salt (C) supplying pyrophosphate ion, and at least one salt (D) for supplying sodium ion and sulfate ion to the composition (step 104);

(3) calculating percent by weight of ferric ion in a molecule of the ferric salt (A), percent by weight of citrate ion in a molecule of the citrate salt (B), and percent by weight of pyrophosphate ion in a molecule of the pyrophosphate salt (C) (step 106);

(4) calculating the amount of the ferric salt (A) needed in the mixing step (step 108) based on the formula:

weight of the ferric salt (A)=the desired weight of
ferric ion/the percent by weight of ferric ion in
a molecule of the ferric salt (A);

(5) calculating the amount of the citrate salt (B) needed in the mixing step (step 110) based on the formula:

weight of the citrate salt (B)=the desired weight of
citrate ion/the percent by weight of citrate ion
in a molecule of the citrate salt (B);

(6) calculating the amount of the pyrophosphate salt (C) needed in the mixing step (step 112) based on the formula:

weight of the pyrophosphate salt (C)=the desired
weight of pyrophosphate ion/the percent by
weight of pyrophosphate ion in a molecule of
the pyrophosphate salt (C);

(7) calculating the amount of sodium ion or sulfate ion contributed by the salts (A), (B) and (C), subtracting these amounts from the total desired percent by weight of sodium ion or sulfate ion to calculate the amount of the salt (D) (step 114);

wherein the order of steps 108 to 112 is changeable among themselves, and wherein the percent by weight (% by weight) is based on an anhydrous basis of the ferric pyrophosphate citrate complex. Instead of using a single salt (D) for providing sodium ion and sulfate ion, multiple salts (D1, D2, D3, etc.) may be used to provide sodium ion and sulfate ions.

In some embodiments, the desired percent by weight of each ion in step 102 may be a ferric ion in an amount from about 7.5 to about 9% by weight, a citrate ion in an amount from about 15 to about 22% by weight, a pyrophosphate ion in an amount from about 15 to about 22% by weight; a sodium ion in an amount from about 18 to about 25% by weight; and a sulfate ion in an amount of from about 20 to about 35% by weight.

In some embodiments, the sum total of percent by weight of pyrophosphate, citrate, ferric, sodium, and sulfate ions is greater than 90%. In some other embodiments, the sum total of percent by weight of pyrophosphate, citrate, ferric, sodium, and sulfate ions is greater than 95%. In further embodiments, the sum total of percent by weight of pyrophosphate, citrate, ferric, sodium, and sulfate ions is 100%. The above weight or % wt. is based on an anhydrous basis of the ferric pyrophosphate citrate complex. The complex contains no or essentially no phosphate ion. Without wishing to be bound by theory, the fact that the total % wt. is may not be 100% can be due to presence of minor impurities (such as sodium carbonate or bicabonate in sodium sulfate, ferric chloride in ferric sulfate) in each salt or due to reasonable calculation errors while rounding off in each specific operation.

The present invention further provides a process for preparing a ferric pyrophosphate citrate complex composition comprising the steps of: designing the ferric pyrophosphate citrate complex composition using the design method; mixing the ferric salt (A), citrate salt (B), the pyrophosphate salt (C), and the fourth salt (D) in their respective calculated amounts in an aqueous based carrier.

Figure 2:
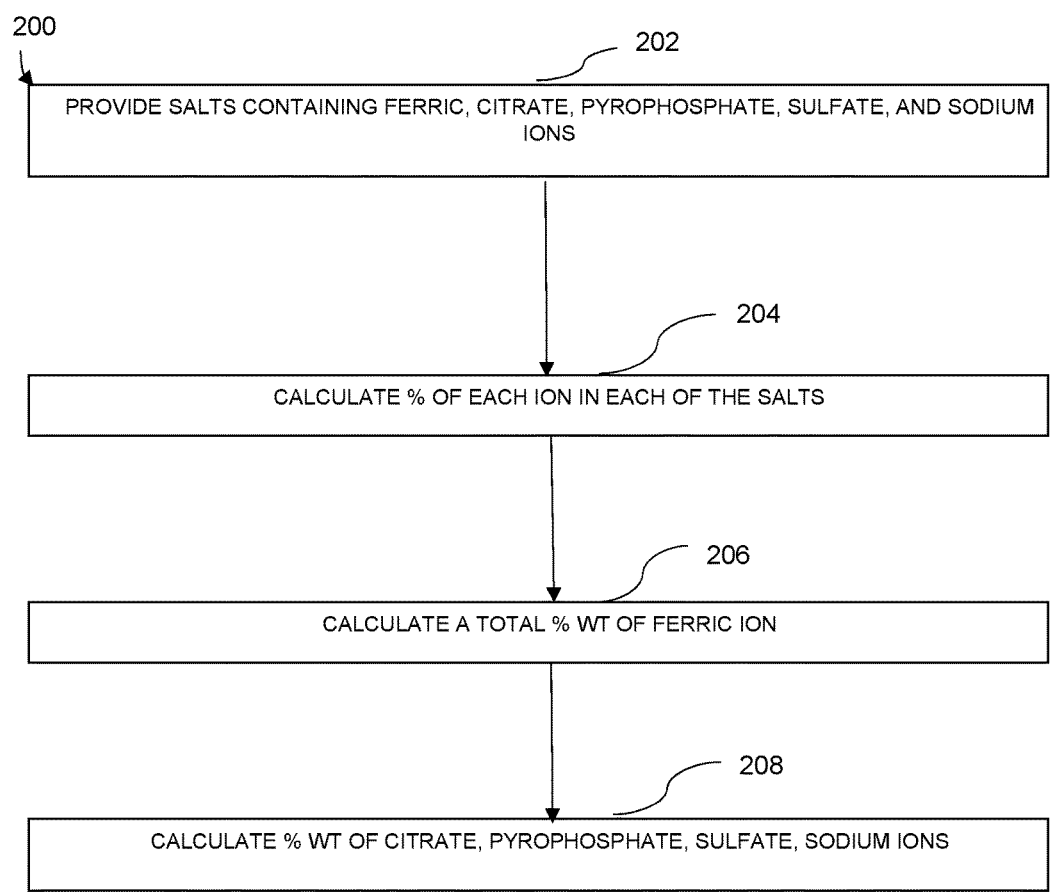
FIG. 2 is a schematic view of a method for determining ion concentrations of a ferric pyrophosphate citrate complex composition.

The present invention also provides a method for determining ion concentrations of a ferric pyrophosphate citrate complex composition, as illustrated in FIG. 2. The method 200 comprises the steps of:
  (a) providing more than one salts, wherein each salt provides at least one of ferric cation, citrate anion, pyrophosphate anion, sulfate anion and sodium cation for preparing a composition (step 202);
  (b) for each salt, calculating percent by weight of cation and percent by weight of anion in a molecule of the salt (step 204);
  (c) based on weight, in percent by weight, of each salt, calculating a total of percent by weight of ferric ion (step 206), using the formula:

A total weight of ferric ion=weight of a first salt
containing ferric ion X the percent by weight of
ferric cation in a molecule of the first salt cal-
culated in step 204+weight of a second salt
containing ferric ion X the percent by weight of
ferric cation in a molecule of the second salt
calculated in step 204, if applicable, +weight of
a third salt containing ferric ion X the percent
by weight of ferric cation in a molecule of the
third salt calculated in step 204, if applicable;

(d) calculating a total of weight of each of citrate anion, pyrophosphate anion, sulfate anion, and sodium cation (step 208) based on the same formula of the above (step 206), except the ferric ion in the formula is to be substituted with the specific anion or cation being calculated;

wherein the weight is based on an anhydrous basis of the ferric pyrophosphate citrate complex.

Figure 3:
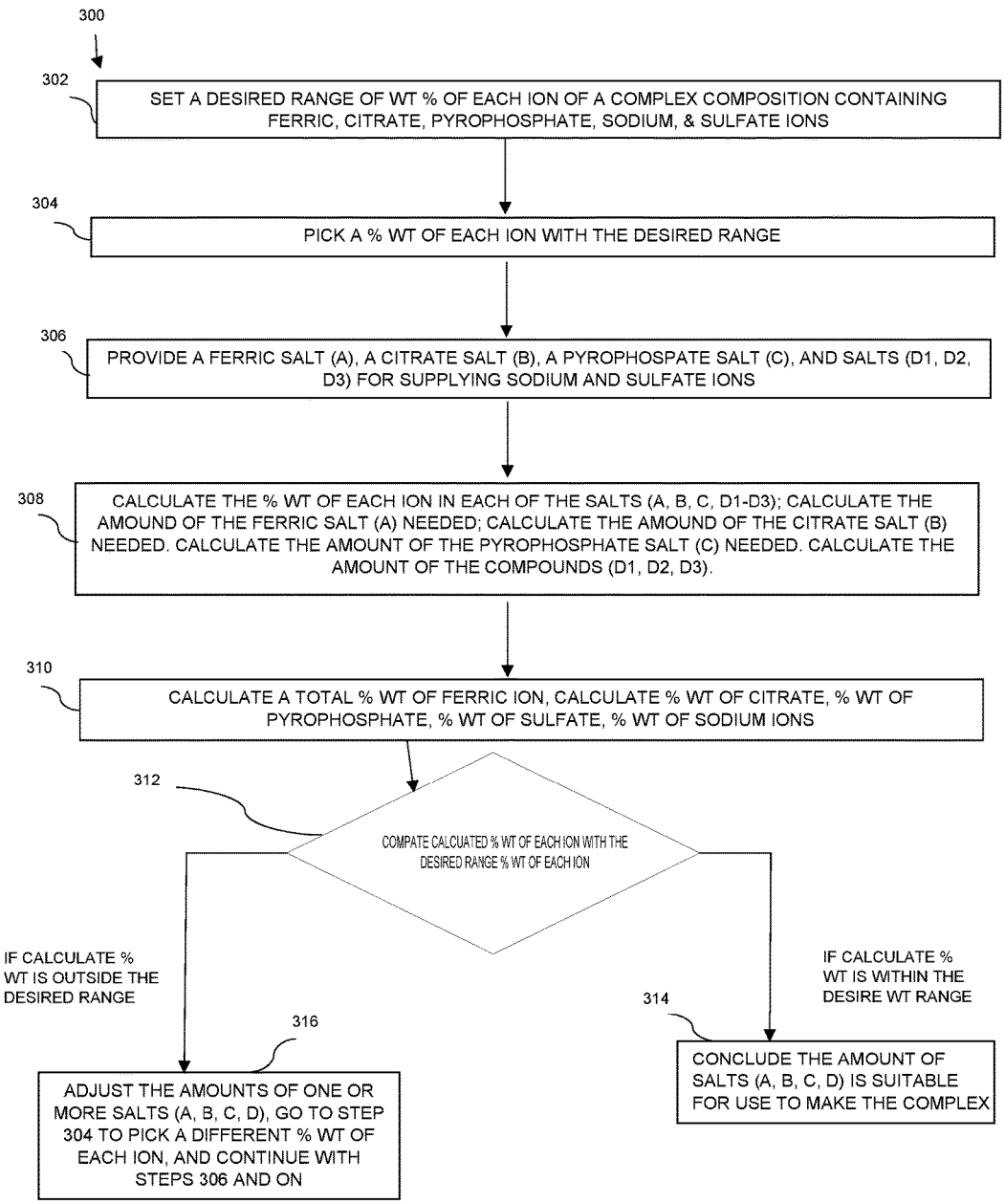
FIG. 3 is a schematic view of a method for designing or adjusting a ferric pyrophosphate citrate complex composition comprising pyrophosphate, citrate, ferric, sodium, and sulfate ions.

Additionally, the present invention also provides a method for adjusting the amount of each salt needed to make a ferric pyrophosphate citrate complex composition so that each ion falls in a preset ion concentration range, as illustrated in FIG. 3. The method 300 comprises the steps of:
  (a) setting a desired range of percent by weight of each ion (step 302);
  (b) picking one percent by weight of each ion within the desired range of percent by weight of said ion (step 304);
  (c) providing one ferric salt (A) for supplying ferric ion, one citrate salt (B) for supplying citrate ion, one pyrophosphate salt (C) supplying pyrophosphate ion, and at least one salt (D) for supplying sodium ion and sulfate ion to the composition (step 306);
  (d) calculating the amounts of salts (A), (B), (C), and (D) needed as described above (step 308);
  (e) based on the amounts of the salts (A), (B), (C), and (D), calculating a total of percent by weight of each ion if the salts (A), (B), (C), and (D) are mixed (step 310);
  (f) comparing (step 312) the calculated total percent by weight of each ion of step 310 with the desired range of percent by weight of each ion set of step 302;
  (g) if the calculated total percent by weight of each and every ion, as calculated in step 310, falls within the desired range of said ion set in step 302, concluding that the amounts of the salts (A), (B), (C), and (D), as calculated in step 308 is suitable for use in preparing the ferric pyrophosphate citrate complex composition—This step is referred as step 314 in FIG. 3; or
    if the calculated total percent by weight of any ion, as calculated in step 310, is outside the desired range of the ion in step 302, adjusting the amounts of one or more of the salts, and repeating steps 304 to 312, until the calculated total percent by weight of each and every ion, as calculated in 310, falls with the desired range of said ion set in 302—This step is referred as step 316 in FIG. 3;

In some embodiments, the desired percent by weight of each ion in step 302 may be a ferric ion in an amount from about 7.5 to about 9% by weight, a citrate ion in an amount from about 15 to about 22% by weight, a pyrophosphate ion in an amount from about 15 to about 22% by weight; a sodium ion in an amount from about 18 to about 25% by weight. The percent by weight of each ion picked in step 304 is in the above referred range of the corresponding ion. In preferred embodiments, the percent by weight of each ion picked in step 304 is in a middle point of the desired range percent by weight of said ion.

Preferably, the above methods can utilize a computer system to automatically calculate the values once one variable is changed. Further, the computer system may have a hardware to allow a user to provide input of variables. The variables may be choices of salts or compounds that provide ion sources, desirable ion concentrations, and the amounts of salts.

The following examples further describe the materials and methods used in carrying out the invention. The examples are not intended to limit the invention in any manner.

Example 1

To 375 ml of water, 8.33 g of tribasic sodium citrate dihydrate, 15.63 g of Sodium pyrophosphate decahydrate, and 3.47 g of sodium sulfate were added. The mixture was stirred at ambient temperature until all the solids dissolved. In another beaker 12.175 g of ferric sulfate was dissolved in 100 ml of water and the brown solution was added to the solution of sodium salts prepared above. The reaction mixture became light green and the pH was 3.8. After heating the reaction at 50° C. for 1.5 hours, the reaction was cooled and diluted with water to a total volume of 500 ml. The pH of this solution was 3.52. The process may further include a step of adjusting the pH value of the solution.

Examples 2-6

Using the equations (1) to (15), the inventors of the application are able to generate spreadsheet files to calculate contribution of each salt to the final composition of each ionic moiety. With these calculations, the inventors of the application can produce any desired solution composition.

Example 2 shows a spreadsheet calculating compositions of Iron PypCitrate complex 1 on anhydrous basis.

|   |   | Ferric Sulfate |   |   |   |   |
|---|---|---|---|---|---|---|
| A | Fe2(SO4)3<br>A = 2F + 3S | Total<br>399.86 | Fe<br>111.69 | 0.2793 | SO4<br>288.19 | 0.7207 |
|   |   | Disodium Citrate |   |   |   |   |
|   | Na2 Citrate<br>B = 2N + 1C | Total<br>236.09 | Na<br>45.98 | 0.1948 | Citrate<br>190.11 | 0.8052 |
|   |   | Sodium Pyrophos |   |   |   |   |
| C | Na2 Pyrophos<br>C = 4N + 1P | Total<br>265.9 | Na<br>91.96 | 0.3458 | Pyrophos<br>173.94 | 0.6542 |
|   |   | Sodium Sulfate |   |   |   |   |
| D | Na2 SO4<br>D = 2N + 1S | Total<br>142.04 | Na<br>45.98 | 0.3237 | SO4<br>96.06 | 0.6763 |
| Total | Weight |   |   |   |   |   |
| A<br>31.33 | 31 | Fe | 8.66 | SO4 | 22.34 |   |
| B<br>24.38 | 25 | Na | 4.87 | Citrate | 20.13 |   |
| C<br>30.03 | 31.5 | Na | 10.89 | Pyrophos | 20.61 |   |
| D<br>9.76 | 12.5 | Na | 4.05 | SO4 | 8.45 |   |
| A + B + C + D = | 100 |   |   |   |   |   |

| Provided |   |   |   |   |   |
|---|---|---|---|---|---|
| Fe | Cit | PyroPhs | SO4 | Na | Total |
| 8.25 | 18.5 | 18.5 | 27.5 | 21.5 | 94.25 |
| 8.75 | 19.63 | 19.63 | 29.18 | 22.81 | 100 |

| Calculated from the table |   |   |   |   |
|---|---|---|---|---|
| Total | Fe | Cit | PyroPhs | SO4 | Na |
| 100.00 | 8.66 | 20.13 | 20.61 | 30.80 | 19.81 |

Example 3 shows a spreadsheet calculating compositions of Iron PypCitrate 2 with 5.5% water to match with the label claim.

|   |   | Ferric Sulfate |   |   |   |   |
|---|---|---|---|---|---|---|
| A | Fe2(SO4)3<br>A = 2F + 3S | Total<br>399.88 | Fe<br>111.69 | 0.2793 | SO4<br>288.19 | 0.7207 |

| | | -continued | | | | | |
|---|---|---|---|---|---|---|---|
| | | | Disodium Citrate | | | | |
| | Na2 Citrate<br>B = 2N + 1C | Total<br>236.09 | Na<br>45.98 | 0.1948 | Citrate<br>190.11 | 0.8052 | |
| | | | Sodium Pyrophos | | | | |
| C | Na2 Pyrophos<br>C = 4N + 1P | Total<br>265.9 | Na<br>91.96 | 0.3458 | Pyrophos<br>173.94 | 0.6542 | |
| | | | Sodium Sulfate | | | | |
| D | Na2 SO4<br>D = 2N + 1S | Total<br>142.04 | Na<br>45.98 | 0.3237 | SO4<br>96.06 | 0.6763 | |
| Total | Weight | | | | | | |
| A<br>31.33 | 29 | Fe | 8.10 | SO4 | 20.90 | | |
| B<br>24.38 | 23 | Na | 4.48 | Citrate | 18.52 | | |
| C<br>30.03 | 29 | Na | 10.03 | Pyrophos | 18.97 | | |
| D<br>9.76 | 13.5 | Na | 4.37 | SO4 | 9.13 | | |
| A + B + C + D = | 94.5 | | | | | | |

| | Target | wt | | Wt should be | About wt |
|---|---|---|---|---|---|
| For Compound-A | | | | | |
| A = 2F + 3S<br>0.2793A + 0.7207A | Fe | 8.25 | A | 29.5372 | |
| For Compound-B | | | | | |
| 2N + 1C<br>0.1948B + 0.8052B | Citrate | 18.5 | B | 22.9744 | |
| For Compound-C | | | | | |
| 4N + 1P<br>0.3458C + 0.6542C | Pyrophos | 18.5 | C | 28.2807 | |
| For Compound-D | | | | | |
| D = 100 − (A + B + C) | | | D | 19.2077 | 100 |

| | | Provided | | | |
|---|---|---|---|---|---|
| Fe | Cit | PyroPhs | SO4 | Na | Total |
| 8.25 | 18.5 | 18.5 | 27.5 | 21.5 | 94.25 |
| 8.75 | 19.63 | 19.63 | 20.18 | 22.81 | 100 |
| | | Calculated from Below table | | | |
| Total | Fe | Cit | PyroPhs | SO4 | Na |
| 94.50 | 8.10 | 18.52 | 18.97 | 30.03 | 18.88 |

Example 4 shows a spreadsheet calculating compositions of Iron PypCitrate 3 by use of Trisodium Citrate to increase amount of Na.

| | | Ferric Sulfate | | | | | |
|---|---|---|---|---|---|---|---|
| A | Fe2(SO4)3<br>A = 2F + 3S | Total<br>399.88 | Fe<br>111.69 | 0.2793 | SO4<br>288.19 | 0.7207 | |
| | | | Trisodium Citrate | | | | |
| | Na3 Citrate<br>B = 3N + 1C | Total<br>258.07 | Na<br>68.97 | 0.2673 | Citrate<br>189.1 | 0.7327 | |
| | | | Sodium Pyrophos | | | | |
| C | Na2 Pyrophos<br>C = 4N + 1P | Total<br>265.9 | Na<br>91.96 | 0.3458 | Pyrophos<br>173.94 | 0.6542 | |

-continued

|   |   | Sodium Sulfate |   |   |   |   |
|---|---|---|---|---|---|---|
| D | Na2 SO4<br>D = 2N + 1S | Total<br>142.04 | Na<br>45.98 | 0.3237 | SO4<br>96.06 | 0.6763 |

|   |   | Sodium Hydroxide |   |   |   |   |
|---|---|---|---|---|---|---|
| E | NaOH<br>E = 1N + 1OH | Total<br>40 | Na<br>23 | 0.5750 | OH<br>17 | 0.4250 |

| Total | Weight |   |   |   |   |
|---|---|---|---|---|---|
| A 31.33 | 29.5 | Fe | 8.24 | SO4 | 21.26 |
| B 24.38 | 25.25 | Na | 6.75 | Citrate | 18.50 |
| C 30.03 | 28.28 | Na | 9.78 | Pyrophos | 18.50 |
| D 9.76 | 9.25 | Na | 2.99 | SO4 | 6.26 |
| E | 3.45 | Na | 1.98 | OH | 1.47 |
| A + B + C + D = | 95.73 |   |   |   |   |

|   | Target | wt |   | Wt should be | About wt |
|---|---|---|---|---|---|
| For Compound-A |   |   |   |   |   |
| A = 2F + 3S<br>0.2793A + 0.7207A | Fe | 8.25 | A | 29.5372 |   |
| For Compound-B |   |   |   |   |   |
| 2N + 1C<br>0.1948B + 0.8052B | Citrate | 18.5 | B | 25.2475 |   |
| For Compound-C |   |   |   |   |   |
| 4N + 1P<br>0.3458C + 0.6542C | Pyrophos | 18.5 | C | 28.2807 |   |
| For Compound-D |   |   |   |   |   |
| 94.25 − (A + B + C)<br>D = 100 − (A + B + C) |   |   | D | 11.1846<br>16.9346 | 100 |

| Provided |   |   |   |   |   |   |
|---|---|---|---|---|---|---|
| Fe<br>7.5-9 | Cit<br>15-22 | PyroPhs<br>15-22 | SO4<br>20-35 | Na<br>18-25 | Phosphate<br><2 | Total |
| 8.25 | 18.5 | 18.5 | 27.5 | 21.5 |   | 94.25 |
| 8.75 | 19.63 | 19.63 | 20.18 | 22.81 |   | 100 |

| Calculated from Below table |   |   |   |   |
|---|---|---|---|---|
| Total | Fe | Cit | PyroPhs | SO4 | Na |
| 94.26 | 8.24 | 18.50 | 18.50 | 27.52 | 21.51 |

Example 5 shows a spreadsheet calculating compositions of Iron PypCitrate 4 by use of NaOH in addition to $Na_2SO_4$.

|   |   |   |   | portion |   | portion |
|---|---|---|---|---|---|---|
|   |   | Ferric Sulfate |   |   |   |   |
| A | Fe2(SO4)3<br>A = 2F + 3S | Total<br>399.88 | Fe<br>111.69 | 0.2793 | SO4<br>288.19 | 0.7207 |
|   |   | Trisodium Citrate |   |   |   |   |
|   | Na3 Citrate<br>B = 3N + 1C | Total<br>258.07 | Na<br>68.97 | 0.2673 | Citrate<br>189.1 | 0.7327 |
|   |   | Sodium Pyrophos |   |   |   |   |
| C | Na2 Pyrophos<br>C = 4N + 1P | Total<br>265.9 | Na<br>91.96 | 0.3458 | Pyrophos<br>173.94 | 0.6542 |

-continued

|   | | | Sodium Sulfate | | | |
|---|---|---|---|---|---|---|
| D | Na2 SO4  D = 2N + 1S | Total  142.04 | Na  45.98 | 0.3237 | SO4  96.06 | 0.6763 |
|   | | | Sodium Hydroxide | | | |
| E | NaOH  E = 1N + 1OH | Total  40 | Na  23 | 0.5750 | OH  17 | 0.4250 |

| | | | Provided | | | |
|---|---|---|---|---|---|---|
| | Fe | Cit | PyroPhs | SO4 | Na | Phosphate |
| | | | Range | | | |
| | 7.5-9 | 15-22 | 15-22 | 20-35 | 18-25 | <2 | Total |
| | 8.25 | 18.5 | 18.5 | 27.5 | 21.5 | | 94.25 |
| | 8.75 | 19.63 | 19.63 | 29.18 | 22.81 | | 100 |

| | | 0 g NaOH | | | |
|---|---|---|---|---|---|
| Total | Weight | | | | |
| A  31.33 | 29.5 | Fe | 8.24 | SO4 | 21.26 |
| B  24.38 | 25.25 | Na | 6.75 | Citrate | 18.50 |
| C  30.03 | 28.25 | Na | 9.77 | Pyrophos | 18.48 |
| D  9.76 | 11.25 | Na | 3.64 | SO4 | 7.61 |
| E | 0 | Na | 0.00 | OH | 0.00 |
| A + B + C + D = | 94.25 | | | | |

| | | Calculated from Below table | | | |
|---|---|---|---|---|---|
| Total | Fe | Cit | PyroPhs | SO4 | Na |
| 94.25 | 8.24 | 18.50 | 18.48 | 28.67 | 20.16 |

| | | 0 g NaOH but increased sodium pyrophosphate | | | |
|---|---|---|---|---|---|
| Total | Weight | | | | |
| A  31.33 | 29.5 | Fe | 8.24 | SO4 | 21.26 |
| B  24.38 | 25.25 | Na | 6.75 | Citrate | 18.50 |
| C  30.03 | 29 | Na | 10.03 | Pyrophos | 18.97 |
| D  9.76 | 10.5 | Na | 3.40 | SO4 | 7.10 |
| E | 0 | Na | 0.00 | OH | 0.00 |
| A + B + C + D = | 94.25 | | | | |

| | | Calculated from Below table | | | |
|---|---|---|---|---|---|
| Total | Fe | Cit | PyroPhs | SO4 | Na |
| 94.25 | 8.24 | 18.50 | 18.97 | 28.36 | 20.18 |

| | | 1 g NaOH | | | |
|---|---|---|---|---|---|
| Total | Weight | | | | |
| A  31.33 | 29.5 | Fe | 8.24 | SO4 | 21.26 |
| B  24.38 | 25.25 | Na | 6.75 | Citrate | 18.50 |
| C  30.03 | 28.25 | Na | 9.77 | Pyrophos | 18.48 |
| D  9.76 | 10.7 | Na | 3.46 | SO4 | 7.24 |

-continued

| | | | | | | | |
|---|---|---|---|---|---|---|---|
| E | 1 | | Na | 0.58 | OH | 0.43 | |
| A + B + C + D= | 94.7 | | | | | | |

| Calculated from Below table | | | | | |
|---|---|---|---|---|---|
| Total | Fe | Cit | Pyrophos | SO4 | Na |
| 94.28 | 8.24 | 18.50 | 18.48 | 28.50 | 20.56 |

| 2 g NaOH | | | | | | |
|---|---|---|---|---|---|---|
| Total | Weight | | | | | |
| A 31.33 | 29.5 | Fe | 8.24 | SO4 | 21.26 | |
| B 24.38 | 25.25 | Na | 6.75 | Citrate | 18.50 | |
| C 30.03 | 28.25 | Na | 9.77 | Pyrophos | 18.48 | |
| D 9.76 | 10.1 | Na | 3.27 | SO4 | 6.83 | |
| E | 2 | Na | 1.15 | OH | 0.85 | |
| A + B + C + D= | 95.1 | | | | | |

| Calculated from Below table | | | | | |
|---|---|---|---|---|---|
| Total | Fe | Cit | PyroPhs | SO4 | Na |
| 94.25 | 8.24 | 18.50 | 18.48 | 28.09 | 20.94 |

| >3 g NaOH (with Exact proportion as required) | | | | | | |
|---|---|---|---|---|---|---|
| Total | Weight | | | | | |
| A 31.33 | 29.5 | Fe | 8.24 | SO4 | 21.26 | |
| B 24.38 | 25.25 | Na | 6.75 | Citrate | 18.50 | |
| C 30.03 | 28.28 | Na | 9.78 | Pyrophos | 18.50 | |
| D 9.76 | 9.25 | Na | 2.99 | SO4 | 6.26 | |
| E | 3.45 | Na | 1.98 | OH | 1.47 | |
| A + B + C + D= | 95.73 | | | | | |

| Calculated from Below table | | | | | |
|---|---|---|---|---|---|
| Total | Fe | Cit | PyroPhs | SO4 | Na |
| 94.26 | 8.24 | 18.50 | 16.50 | 27.52 | 21.51 |

Example 6 shows a spreadsheet calculating compositions of Iron PypCitrate 5 by use of Ferric Citrate and Ferric Pyrophosphate.

| | | | | portion | | portion |
|---|---|---|---|---|---|---|
| | | | Ferric Sulfate | | | |
| A | Fe2(SO4)3 A = 2F + 3S | Total 399.88 | Fe 111.69 | 0.2793 | SO4 288.19 | 0.7207 |
| | | | Trisodium Citrate | | | |
| | Na3 Citrate B = 3N + 1C | Total 258.07 | Na 68.97 | 0.2673 | Citrate 189.1 | 0.7327 |
| | | | Sodium Pyrophos | | | |
| C | Na2 Pyrophos C = 4N + 1P | Total 265.9 | Na 91.96 | 0.3458 | Pyrophos 173.94 | 0.6542 |
| | | | Sodium Sulfate | | | |
| D | Na2 SO4 D = 2N + 1S | Total 142.04 | Na 45.98 | 0.3237 | SO4 96.05 | 0.6763 |

| | | | Sodium Hydroxide | | | |
|---|---|---|---|---|---|---|
| E | NaOH<br>E = 1N + 1OH | Total<br>40 | Na<br>23 | 0.5750 | OH<br>17 | 0.4250 |
| | | | Ferric Pyrophosphate | | | |
| F | Fe4 Pyrophos<br>F = 4F + 3P | Total<br>745.21 | Fe<br>223.38 | 0.2998 | Pyrophos<br>521.83 | 0.7002 |
| | | | Ferric Citrate | | | |
| G | Fe Citrate (C6H<br>G = 1F + 1C | Total<br>244.94 | Fe<br>55.845 | 0.2280 | Citrate<br>189.1 | 0.7720 |

| | | | Provided | | | |
|---|---|---|---|---|---|---|
| Fe | Cit | PyroPhs | SO4 | Na | Phosphate | |
| | | | Range | | | |
| 7.5-9 | 15-22 | 15-22 | 20-35 | 18-25 | <2 | Total |
| 8.25 | 18.5 | 18.5 | 27.5 | 21.5 | | 94.25 |
| 8.75 | 19.63 | 19.63 | 29.18 | 22.81 | | 100 |

Ferric Citrate & Ferric Sulfate

| Total | Weight | | | | |
|---|---|---|---|---|---|
| Fe2(SO4)3 | 9.95 | Fe | 2.78 | SO4 | 7.17 |
| Na3 Citrate | 0 | Na | 0.00 | Citrate | 0.00 |
| Na2 Pyrophos | 28.25 | Na | 9.77 | Pyrophos | 18.48 |
| Na2 SO4 | 32.05 | Na | 10.37 | SO4 | 21.68 |
| NaOH | 0 | Na | 0.00 | OH | 0.00 |
| Fe4 Pyrophos | 0 | Fe | 0.00 | Pyrophos | 0.00 |
| Fe Citrate (C6H5FeO7) | 24 | Fe | 5.47 | Citrate | 18.53 |
| Total wt= | 94.25 | | | | |

Calculate from Below table

| Total | Fe | Cit | PyroPhs | SO4 | Na |
|---|---|---|---|---|---|
| 94.25 | 8.25 | 18.53 | 18.48 | 28.85 | 20.15 |

Ferric pyrophosphate

| Total | Weight | | | | |
|---|---|---|---|---|---|
| Fe2(SO4)3 | 0 | Fe | 0.00 | SO4 | 0.00 |
| Na3 Citrate | 25.25 | Na | 6.75 | Citrate | 18.50 |
| Na2 Pyrophos | 0 | Na | 0.00 | Pyrophos | 0.00 |
| Na2 SO4 | 41.5 | Na | 13.43 | SO4 | 28.07 |
| NaOH | 0 | Na | 0.00 | OH | 0.00 |
| Fe4 Pyrophos | 27.51 | Fe | 8.25 | Pyrophos | 19.26 |
| Fe Citrate (C6H5FeO7) | 0 | Fe | 0.00 | Citrate | 0.00 |
| Total wt= | 94.26 | | | | |

Calculated from Below table

| Total | Fe | Cit | PyroPhs | SO4 | Na |
|---|---|---|---|---|---|
| 94.26 | 8.25 | 18.50 | 19.26 | 28.07 | 20.18 |

Ferric Sulfate

| Total | Weight | | | | |
|---|---|---|---|---|---|
| Fe2(SO4)3 | 29.5 | Fe | 8.24 | SO4 | 21.26 |
| Na3 Citrate | 25.25 | Na | 6.75 | Citrate | 18.50 |
| Na2 Pyrophos | 28.25 | Na | 9.77 | Pyrophos | 18.48 |
| Na2 SO4 | 11.25 | Na | 3.64 | SO4 | 7.61 |
| NaOH | 0 | Na | 0.00 | OH | 0.00 |
| Fe4 Pyrophos | 0 | Fe | 0.00 | Pyrophos | 0.00 |

-continued

| | | | | | | |
|---|---|---|---|---|---|---|
| Fe Citrate (C6H5FeO7) | 0 | Fe | 0.00 | Citrate | 0.00 | |
| Total wt= | 94.25 | | | | | |

| Calculated from Below table | | | | | |
|---|---|---|---|---|---|
| Total | Fe | Cit | PyroPhs | SO4 | Na |
| 94.25 | 8.24 | 18.50 | 18.48 | 28.87 | 20.16 |

While the present teachings have been described above in terms of specific embodiments and examples, it is to be understood that they are not limited to those disclosed embodiments and examples. Many modifications to the embodiments and examples will come to mind to those skilled in the art to which this pertains, and which are intended to be and are covered by both this disclosure and the appended claims. It is intended that the scope of the present teachings should be determined by proper interpretation and construction of the appended claims and their legal equivalents, as understood by those of skill in the art relying upon the disclosure in this specification and the attached drawings.

What is claimed is:

1. A process for directly preparing a liquid pharmaceutical dosage form of ferric pyrophosphate citrate complex composition comprising:
    mixing a citrate ion source, a pyrophosphate ion source, a sodium ion source, and a ferric ion source in an aqueous based vehicle carrier to form a mixture having an acidic pH;
    heating the mixture above room temperature to form a solution;
    cooling the heated solution to room temperature or below without isolation of a solid form of ferric pyrophosphate citrate complex; and
    adding water to the cooled solution to adjust the ferric ion concentration to about 10 to 250 mM.

2. The process of claim 1, wherein the mixing step further comprises a sulfate ion source, and wherein the ferric pyrophosphate citrate complex composition further comprises a sulfate ion.

3. The process of claim 2, wherein the sulfate ion is provided by up to three different sulfate compounds.

4. The process of claim 1,
    wherein the ferric ion source is selected from a group consisting of ferric sulfate, ferric sulfate hydrate, ferric chloride, ferric ammonium sulfate, a hydrate thereof, and a combination thereof;
    wherein the citrate ion source is selected from a group consisting of citric acid, monosodium citrate, disodium citrate, trisodium citrate, a hydrate thereof, and a combination thereof; and
    wherein the pyrophosphate ion source is selected from a group consisting of disodium dihydrogen pyrophosphate, tetrasodium pyrophosphate, a hydrate thereof, and a combination thereof.

5. The process of claim 2,
    wherein the ferric ion is present in an amount from about 7.5 to about 9% by weight, the citrate ion is present in an amount from about 15 to about 22% by weight, the pyrophosphate ion is present in an amount from about 15 to about 22% by weight,
    the sodium ion is present in an amount from about 18 to about 25% by weight
    the sulfate ion is present in an amount of from about 20 to about 35% by weight, and the composition contains less than 2% by weight of phosphate ion,
    said percent by weight is based on an anhydrous basis of the total ions added into the aqueous based vehicle carrier.

6. The process of claim 1, wherein the sodium ion source is provided by up to three different compounds.

7. A pharmaceutical composition comprising a ferric pyrophosphate citrate complex prepared by the process of claim 1.

8. A process for directly preparing a liquid pharmaceutical dosage form of ferric pyrophosphate citrate complex composition comprising:
    setting a desired percent by weight range of ferric ion, citrate ion, and pyrophosphate ion;
    selecting one ferric salt (A) for providing the ferric ion, one citrate salt (B) for providing the citrate ion, and one pyrophosphate salt (C) for providing the pyrophosphate ion;
    calculating percent by weight of the ferric ion in a molecule of the ferric salt (A), percent by weight of the citrate ion in a molecule of the citrate salt (B), and percent by weight of the pyrophosphate ion in a molecule of the pyrophosphate salt (C);
    calculating the amount of the ferric salt (A) needed in a mixing step based on the formula: weight of the ferric salt (A)=the desired weight of ferric ion/the percent by weight of ferric ion in a molecule of the ferric salt (A);
    calculating the amount of the citrate salt (B) needed in the mixing step based on the formula: weight of the citrate salt (B)=the desired weight of citrate ion/the percent by weight of citrate ion in a molecule of the citrate salt (B);
    calculating the amount of the pyrophosphate salt (C) needed in the mixing step based on the formula: weight of the pyrophosphate salt (C)=the desired weight of pyrophosphate ion/the percent by weight of pyrophosphate ion in a molecule of the pyrophosphate salt (C);
    mixing A, B, and C in an aqueous based vehicle carrier to form a mixture having an acidic pH;
    heating the mixture above room temperature to form a solution;
    cooling the heated solution to room temperature or below without isolation of a solid form of ferric pyrophosphate citrate complex; and
    adding water to the cooled solution to adjust the ferric ion concentration to about 10 to 250 mM; and
    wherein said desired percentages by weight are based on an anhydrous basis of the total ions added into the aqueous based vehicle carrier.

9. The method of claim 8, wherein the desired range of ferric ion is about 7.5 to about 9% by weight, the desired range of citrate ion is from about 15 to about 22% by weight, and the desired range of pyrophosphate ion from about 15 to about 22% by weight.

10. The method of claim 8, further comprising the steps of
   setting a desired percent by weight range of sodium ion,
   setting a desired percent by weight of range sulfate ion,
   selecting up to three additional compounds (D1, D2, D3) for providing the sodium ion and sulfate ion,
   calculating the amount of sodium ion or sulfate ion contributed by the salts (A), (B) and (C), subtracting these amounts from the total desired percent by weight of sodium ion or sulfate ion to calculate the amount of the compounds (D1, D2, D3), and
   mixing the compounds D1, D2, D3 with the citrate ion source, pyrophosphate ion source, and a ferric ion source in the aqueous based vehicle carrier.

11. The method of claim 10, wherein the total percent by weight of pyrophosphate, citrate, ferric, sodium, and sulfate ions is greater than 90%.

12. The method of claim 10, wherein the desired range of sodium ion is from about 18 to about 25% by weight, and the desired range of sulfate ion from about 20 to about 35% by weight.

13. The method of claim 8, further comprising the step of designing a computer program to automate the process, wherein the process further comprises a step for allowing a user to input the amounts of one or more of the salts.

* * * * *